United States Patent [19]

Yoshimoto et al.

[11] Patent Number: 5,214,014

[45] Date of Patent: May 25, 1993

[54] DEODORIZING CATALYST

[75] Inventors: Masafumi Yoshimoto, Sakai; Tadao Nakatsuji, Nara; Kazuhiko Nagano; Kimihiko Yoshida, both of Sakai, all of Japan

[73] Assignee: Sakai Chemical Industry Co., Ltd., Sakai, Japan

[21] Appl. No.: 684,093

[22] Filed: Apr. 12, 1991

Related U.S. Application Data

[63] Continuation-in-part of Ser. No. 412,058, Oct. 10, 1989, abandoned.

[30] Foreign Application Priority Data

Sep. 26, 1988 [JP] Japan ................... 63-240549
Nov. 28, 1988 [JP] Japan ................... 63-301404
Dec. 28, 1988 [JP] Japan ................... 63-334349
Feb. 28, 1991 [JP] Japan ................... 3-120656

[51] Int. Cl.$^5$ .................. B01J 21/06; B01J 21/16; B01J 23/16; B01J 23/72; B01J 23/74
[52] U.S. Cl. ...................... 502/84; 502/182; 502/184; 502/185; 502/241; 502/324; 502/325; 502/330; 502/338; 502/345
[58] Field of Search ............... 502/84, 182, 184, 185, 502/241, 324, 325, 330, 338, 345

[56] References Cited

U.S. PATENT DOCUMENTS 4,416,800 11/1983 Abe et al. ................... 502/184 X
5,070,064 12/1991 Hsu et al. ................... 502/325

FOREIGN PATENT DOCUMENTS 54-2288 1/1979 Japan ................... 502/184

Primary Examiner—W. J. Shine
Attorney, Agent, or Firm—Nikaido, Marmelstein, Murray & Oram

[57] ABSTRACT

The present invention provides a deodorizing method for removing malodorant components by oxidative destruction with ozone in the presence of a catalyst comprising a first component, which is a metal oxide, and a second component which is at least one member selected from the group consisting of titanium dioxide, silver oxide, silica and gold, or a catalyst comprising manganese dioxide and clay.

Also, the present invention provides a deodorizing catalyst having its active components carried in a layer, having a thickness of 10 to 200 μm, on the carrier, thereby stably removing malodorant components at a high rate, even when the reaction conditions are changed.

8 Claims, 1 Drawing Sheet

DEODORIZING CATALYST

This is a Continuation-in-Part of Ser. No. 412,058 filed on Oct. 10, 1989 now abandoned.

BACKGROUND OF THE INVENTION

The present invention relates to a deodorizing method for destroying compounds which emit an offensive smell and which are contained in a gas or the like (hereinafter referred to as malodorant components), and to deodorizing catalysts for using of this method.

Examples of a conventional method of destroying the malodorant components contained in gas, include (i) an adsorptive deodorizing method using a porous substance such as activated carbon, zeolite or the like, (ii) a wet-treatment deodorizing method using an oxidizing agent or a reducing agent, or (iii) an ozonolysis deodorizing method and the like.

However, any of the conventional deodorizing methods above mentioned (hereinafter referred to as conventional methods) do not fully achieve satisfactory deodorizing.

More specifically, in the adsorptive deodorizing method, the adsorbent needs to be regenerated or the like since its adsorbing ability expires in a limited period of time. This presents the problem that the deodorizing apparatus requires much labor and expense for maintenance.

The wet treatment deodorizing method involves a troublesome treatment of additives such as an oxidizing agent or the like.

Finally, the ozonolysis deodorizing method includes no such problems as above mentioned, but requires decomposition of ozone admixed with the gas submitted to deodorizing. Sometimes there is insufficient removal of the malodorant components by oxidative destruction and therefore there may be insufficient prevention of environmental pollution, which may provoke respiratory disease or the like.

A solid type catalyst which may be wholly shaped of the catalytic active ingredient, e.g. manganese, titanium and clay in the form of a honeycomb, was used as an oxidative destruction catalyst to remove the malodorant components in an ozonolysis deodorizing method. Accordingly with conventional solid catalyst, however, since the saturated absorption of malodorant components in relation to the catalyst is large, when a condition change occurs, such as in a refrigeration or the like, for example, or when the reaction temperature rises, the concentration of malodorant components becomes low, the malodorant components are released from the catalyst to the air, and, as a result, concentration of malodorant components in the air is increased.

When a gas to be deodorized contains fractions of acid substances, such as nitrogen oxides, lower fatty acids and the like, the acid substances may accumulate on or in the catalyst, or may react with the catalytic components thereof so that the catalyst is deteriorated to an extent such that malodorant components are released in the supposedly deodorized gas.

SUMMARY OF THE INVENTION

An object of this invention is to provide a catalyst for use in deodorization, which can reduce the thickness of the layer of catalytically active components provided on the carrier, and which is excellent in its capability to destroy malodorant components and in its durability.

To achieve the objects above mentioned, the catalyst of this invention is adapted to remove malodorant components by oxidative destruction with ozone, and comprises a carrier, and active components carried on the carrier in the range from 10 to 200 μm of thickness.

Examples of the active components include (i) at least one metal oxide, the metal of which is selected from the group consisting of copper, manganese, cobalt, iron and nickel, and (ii) at least one member selected from the group consisting of titanium dioxide, silver oxide, silica, and gold, or comprising manganese dioxide and clay.

DETAILED DESCRIPTION OF THE INVENTION

Figure 1:
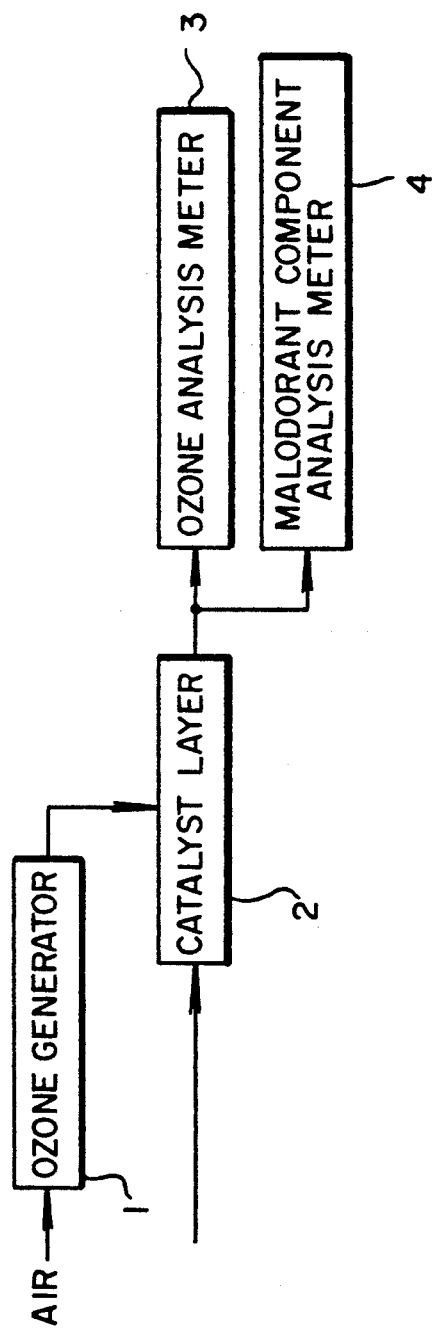
FIG. 1 is a flowsheet of a catalyst activity test implied in Examples.

Examples of the malodorant components to be removed by the present method include ammonia, trimethyl amine, hydrogen sulfide, methyl mercaptan, methyl sulfide, methyl disulfide, acetaldehyde, styrene, methyl ethyl ketone, acrolein, propionaldehyde, butyl alcohol, phenol, cresol, diphenyl ether, acetic acid, propionic acid, n-pentanoic acid, methylamine, dimethylamine, skatole, dimethylthioether, dimethyl mercaptan, hydrogen chloride and allyl chloride.

The present method may be used for deodorizing an exhaust gas discharged, for example, from sewage disposal plants, refuse disposal plants, printing factories, plating factories, general chemical factories and the like.

The catalyst comprising (i) at least one metal oxide, the metal of which is selected from the group consisting of copper, manganese, cobalt, iron and nickel, and (ii) at least one member selected from the group consisting of titanium dioxide and silver oxide, and gold, includes binary-catalysts such as $MnO_2$-$TiO_2$, $CuO$-$TiO_2$, $Co_3O_4$-$TiO_2$, $FeO_2O_3$-$TiO_2$ and $Fe2O3$-$Au$, and ternary catalysts such as $MnO_2$-$Co_3O_4$-$TiO_2$, $CuO$-$MnO_2$-$Ag_2O$, $MnO_2$-$Co_3O_4$-$Ag_2O$, $NiO$-$MnO_2$-$TiO_2$, or the like.

A preferable concentration (% by weight) of the first metal oxide (i) is in a range from 25 to 95%, as converted into the concentration of the metal alone. When the concentration of the first metal oxide (i) is less than 25%, as converted into the concentration of the metal alone, the catalyst is not sufficiently effective in removing the malodorant components. When the concentration of the first metal oxide (i) is more than 95%, as converted into the concentration of the metal alone, the catalyst does not have enough durability.

A preferable concentration (% by weight) of the second component (ii) is in the range from 5 to 75%, as converted into the concentration of the metal(s) alone. When the concentration of the second component is less than 5%, as converted into the concentration of the metal alone, the catalyst does not have enough durability. When the concentration of the second component (ii) is more than 75%, as converted into the concentration of the metal alone, the catalyst is not sufficiently effective in removing the malodorant components.

In the catalyst comprising of manganese dioxide and clay, or manganese oxide, clay and titanium dioxide, a preferably concentration (% by weight) of the manganese dioxide is in the range from 20 to 90%. When concentration of the manganese dioxide is less than 20%, the catalyst does not have enough active component. When concentration of the manganese dioxide is more than 90%, capacity of the catalyst is not improved in proportion to addition of manganese dioxide.

Also, the capacity of above mentioned catalyst is improved by substituting a part of the manganese with at least one metal oxide, the metal of which is selected from the group consisting of Cu, Co, Fe, Ni and Ag. A preferably ratio of this substitution, as converted into oxide, is in a range from 1 to 30%. When the substitution is less than 1%, the capacity of the catalyst is not improved. When the substitution is more than 30%, capacity of the catalyst is not improved in proportion to the substitution.

The substituted catalyst mentioned above, includes $MnO_2$-CuO-clay, $MnO_2$-$Co_3O_4$-clay, $MnO_2$-$Fe_2O_3$-clay, $MnO_2$-NiO-clay, $MnO_2$-$Ag_2O$-clay, $MnO_2$-CuO-clay-$TiO_2$, $MnO_2$-$Co_3O_4$-clay-$TiO_2$, $MnO_2$-$Fe_2O_3$-clay-$TiO_2$, $MnO_2$-NiO-clay-$TiO_2$, $MnO_2$-$Ag_2O$-clay-$TiO_2$ and the like. The above mentioned clay is suitably a bedded clay mineral which is mainly composed of pyrophyllite, talc, mica, chlorite, montmorillonite, kaolin, halloysite and the like. Examples of the clay are Kibushi clay, Gairome clay or the like.

The catalyst for use in the present method is not particularly limited in shape, but may be in any form such as honeycomb, pellet, cylinder, plate, pipe or the like.

The concentration (% by weight) of active components contained in the catalyst of this invention is preferably 50% or more, and more preferably 75% or more. When the concentration of the active components in the catalyst is less than 50%, the catalyst cannot sufficiently remove the malodorant components.

The catalyst may be manufactured by any known method suitably selected from impregnation, kneading, coprecipitation precipitation, oxide mixing and the like. In production of the catalyst, there may be added (i) a forming assistant such that the catalyst is easily molded into an appropriate shape, or (ii) a reinforcing agent, such as inorganic fiber or an organic binder, to improve its mechanical strength, or the like.

Also, the catalyst of this invention can be produced by supporting active components on the carrier. The carrier is not particularly limited in shape, but may be in any form, such as honeycomb, pellet, cylinder, plate, pipe or the like. The carrier is not particularly limited in material, but may, for example, e made of urethane foam, clay or the like.

The preferable thickness of the active components on the carrier is in the range from 10 to 200 $\mu$m. When the thickness is in that range, saturated absorption amount of malodorant components in the catalyst is adjusted appropriately. Accordingly, the catalyst presents a stable removing rate of the malodorant component, even if the reaction conditions change, e.g. raising the reaction temperature, lowering the concentration of malodorant components, or the like. When the thickness of active components is more than 200 $\mu$m, the saturated absorption amount of the malodorant components in the catalyst is too much. Thus, when the reaction condition change, as above mentioned, the malodorant compound absorbed in the catalyst will be released from the catalyst to the air. As a result, the catalyst becomes a generator of stench. When the thickness of the active components is less than 10 $\mu$m, the catalyst does not have enough capacity for removing the malodorant components.

A suitable amount of ozone ($O_3$), which is used together with the catalyst at the time of deodorizing, depends on the types and concentrations of malodorant components to be removed, the reaction temperature, the type and amount of the catalyst, and the like. For example, when a gas, containing $H_2S$ as the malodorant component, is to be deodorized, it is preferable that 1 to 2 moles of $O_3$ coexists per mol of $H_2S$. For a gas containing $NH_3$ as the malodorant component, it is preferable that 1 to 3 mols of $O_3$ coexists per mol of $NH_3$. For a gas containing methyl mercaptan as the malodorant component, it is preferable to use 1 to 4 mol of $O_3$ per mol of methyl mercaptan.

If the gas to be deodorized contains malodorant components in a high concentration, the concentration $O_3$ may exceed the preferable range above mentioned in order to improve the rate of removal of malodorant component. However, excess surplus $O_3$ may remain after deodorizing. Accordingly, attention should be paid such that substantially no excess $O_3$ coexists. This will act to prevent the generation of such residue.

The reaction temperature at the time of deodorizing is preferably in a range of from 0° to 40° C., and more preferably in a range of from 10° to 30° C. A temperature of less than 0° C. causes the reaction speed to be slower, while a temperature exceeding 40° C. requires an addition of energy to increase the temperature, resulting in poor economy.

Preferably, the catalyst comes into contact with the reaction gas in a range of area velocity (AV) from 5 to 50. An area velocity of less than 5 requires a greater amount of catalyst, while an area velocity exceeding 50 causes the decomposition efficiency to be lowered whereby failing to achieve the desired decomposition efficiency. It is here noted that the area velocity refers to a value obtained by dividing the reaction amount ($Nm^3/u, u:Hr$) by the gas contact area per catalyst unit volume ($m^2/m^3$).

Another catalyst for use in deodorizing according to this invention comprises a carrier containing activated carbon, and active components carried on the carrier in a thickness of 5 to 100 $\mu$m sufficient for promoting destruction of malodorant components with ozone.

The inventors have found that since the deodorizing reaction proceeds only on the catalyst surface, because a rate-determining step of the reaction is the step of dispersion of the gas into catalytic solid, a preferable structure of the catalyst may be a "coating type" obtained by supporting the catalytic active components near the surface of a suitable support means. This coating-type catalyst, however, has a problem that, for example, as a honeycomb structure has an increasing number of cells/inch$^2$, it becomes more difficult to produce the honeycomb catalyst.

On the other hand, the catalyst wherein the carrier contains activated carbon therein as described above allows a reduction in the thickness of the coating of the active components. Accordingly, the catalyst provided by this invention is superior in productivity to a molded catalyst, especially a honeycomb catalyst having a small pitch. It is also superior in deodorizing capability and durability.

Examples of the catalytic active components having deodorization capability with ozone are at least one metal, at least one metal oxide, or at least one metal sulfate, the metal of which is selected from a group consisting of Ti, Cu, Mn, Ni, Fe, Ag, Au, Mo, Zr, Sn, Nb and W; and or the components may contain activated carbon or acid clay. The metal oxides to be carried includes those mainly comprising $MnO_2$, $NiO$, $CuO$ or $Fe_2O_3$; those mainly comprising $MnO_2$-$TiO_2$, $MnO_2$-$CuO$, $MnO_2$-$Fe_2O_3$; those mainly comprising $MnO_2$-$TiO_2$, $MnO_2$-$CuO$, $MnO_2$-$Fe_2O_3$, $MnO_2$-$Ag_2O$, $NiO$-$Co_3O_4$, $NiO$-$TiO_2$, $NiO$-$MnO_2$, $NiO$-$Ag_2O$, $NiO$-$MoO_3$, $NiO$-$WO_3$, $NiO$-$SnO_2$; and those mainly comprising $MnO_2$-$Ag_2O$-$TiO_2$, $MnO_2$-$CuO$-$Ag_2O$, $NiO$-$MnO_2$-$Ag_2O$, and $NiO$-$MnO_2$-$TiO_2$, which have already been set forth by the inventors.

The form of the catalyst is not particularly limited and may be in any form, such as honeycomb and the like, as described above.

A carrier containing activated carbon may be produced by a kneading method in general. A preferable concentration of activated carbon contained in said carrier is 10% by weight or more, and more preferably 20% by weight or more. When the concentration is less than 10% by weight, the destruction capability with ozone may be considerably lowered, and therefore it would be required to increase a thickness of the coating to maintain a high destruction capability. The catalytically active components carried on these carriers may be produced by a method such as a wash-coat method, or the like. A preferable coating thickness is 5 to 100 μm, and more preferably 10 to 50 μm. When the thickness is less than 5 μm, the destruction activity of the catalyst may deteriorate. When the thickness is more than 100 μm, the destruction activity thereof may not be improved but only the pressure drop increased.

EXAMPLES

The following description will discuss, in more detail, examples of the present invention. It is noted that the present invention should not be limited to the following examples.

EXAMPLE 1

Kibusushi clay was dried for 18 hours at 100° C., whereupon it was crushed in a sample mill having a 0.5 mm/φ screen. 20 kg of the resulting product was mixed with 1 kg of methyl cellulose type binder (Yuken Industry Co., YB-32) and water. The mixture was kneaded thoroughly by a neader. After that, the mixture was put into an orga-screw type extruder, to produce a honeycomb. In such a case, the water content was adjusted so as to have 30-35 kg/cm² of pressure. The obtained honeycomb was air-dried at ambient temperature, and it was heated up to 500° C. at a rate of 5° C. per hour. After it was kept at 500° C. for 3 hours, it was cooled down at a rate of 10° C. per hour. Thus, a honeycomb type carrier having an open area of 64% and a pitch of 4.0 mm was obtained.

704 g of $MnO_2$, having a specific surface area of 48 m²/g, was added to 1034 ml of a titania sol ($TiO_2$ concentration : 150 g/l). To the mixture, 250 g of glass beads was added to adjust the degree of milling. The resultant mixture was agitated and mixed for 30 minutes. The glass beads were separated from the mixture to produce a slurry. After the slurry was diluted with 300 ml of water, the slurry was impregnated into the corrugated honeycomb. The excess slurry was removed from the honeycomb, and the honeycomb was air-dried and baked. Thus, there was prepared a binary-catalyst carrying 10 μm in thickness of $MnO_2$-$TiO_2$ (weight ratio of 82:18) which represented a carry weight of 43%. The open area of the catalyst was 63%, and the area available for contact with gas (hereinafter referred to as Ap) was 795 m²/m³. The thickness of the $MnO_2$-$TiO_2$ was measured by electron probe micro analyzer (EPMA).

EXAMPLE 2

There was prepared a binary-catalyst, carrying $MnO_2$-$TiO_2$ having an open area of 60% and an Ap 775 m²/m³, in the same manner as that set forth in Example 1, except that in this Example 2 the carry weight of the catalyst was 26.5% and the average thickness of the $MnO_2$-$TiO_2$ layer was about 50 μm.

EXAMPLE 3

There was prepared a binary-catalyst carrying $MnO_2$-$TiO_2$ having an open area of 56% and an Ap 750 m²/m³, in the same manner as set forth in Example 1, except that in this Example 3 the $MnO_2$-$TiO_2$ sol slurry was not diluted with water, the average carry weight of catalyst was 40.7% and the average thickness of the $MnO_2$-$TiO_2$ layer was about 100 μm.

EXAMPLE 4

There was prepared a binary-catalyst carrying $MnO^2$-$TiO_2$ having an open are of 49% and an Ap 700 m²/m³, in the same manner as that set forth in Example 1, except that in this Example 4, the $MnO_2$-$TiO_2$ sol slurry was not diluted with water, the carry weight of the catalyst was 65.1% and the average thickness of $MnO_2$-$TiO^2$ was about 200 μm.

COMPARATIVE EXAMPLE 1

There was prepared a binary-catalyst carrying $MnO_2$-$TiO_2$ having an open area of 64% and an Ap 798 m²/m³, in the same manner as set forth in Example 1, except that in this Comparative Example 1, the carry weight of the catalyst was 2.2% and the average thickness of the $MnO_2$-$TiO_2$ layer was about 5 μm.

COMPARATIVE EXAMPLE 2

There was prepared a binary-catalyst carrying $MnO_2$-$TiO_2$ having an open area of 46% and an Ap 675 m²/m³, in the same manner as set forth in Example 1, except that in this Comparative Example 2, the $MnO^2$-$TiO^2$ sol slurry was not diluted with water, the carry weight of the catalyst was 72.8% and the average thickness of the $MnO_2$-$TiO^2$ layer was about 250 μm.

Catalyst Activity Test

Each catalyst of Examples 1 to 4 and Comparative Examples 1 and 2 were submitted to a catalyst activity test with the use of the test method having a flowsheet as shown in FIG. 1, under reaction conditions discussed later.

In FIG. 1, malodorant components $H_2S$, $NH_3$ and methyl amine contained in a gas to be deodorized are introduced into contact with a catalyst layer 2. The malodorant components thus introduced are decomposed by ozone $O_3$ introduced from an ozone generator 1 into contact with the catalyst layer 2. A portion of the gas, after being decomposed and deodorized, is introduced into an ozone analyzer 3, in which the remaining ozone $O_3$ is subjected to quantitative analysis. The remaining portion of the gas, after being decomposed and deodorized, is introduced into a malodorant component analysis meter 4 including two gas chromatographs (designed for analyzing $H_2S$ or methyl amine) and one $NH_3$ meter. These devices are adapted to carry out quantitative analysis of malodorant components.

| (Reaction Conditions I) | |
| --- | --- |
| Space velocity | 20,000/Hr |
| Reaction temperature | 20° C. |
| Concentration of malodorant components/ Concentration of ozone components: | |
| H₂S/ozone | 10/20 ppm |
| NH₃/ozone | 10/30 ppm |
| methyl mercaptan/ozone | 5/10 ppm |

Reaction Conditions II

After the catalyst Activity Test was carried out for 24 hours under Reaction Condition I, the reaction temperature was raised to 50° C. After 5 minutes, the concentrations of the malodorant components and the ozone were measured.

Reaction Conditions III

After the catalyst Activity Test was carried out for 24 hours under Reaction Condition I, the concentration of the malodorant components was changed as set forth below:

concentration of $H_2S$:1 ppm
concentration of $NH_3$:1 ppm
concentration of methyl mercaptan:1 ppm After 5 minutes, concentrations of the malodorant components and the ozone were measured.

The test results are shown in the Table 1.

utes. The glass beads were separated from the mixture to produce a slurry. After the slurry was diluted with 300 ml of water, the slurry was impregnated into the same honeycomb as that used in Example 1. The excess slurry was removed from the honeycomb, and the honeycomb was air-dried and baked. Thus, there was prepared a binary-catalyst carrying $MnO_2$-$SiO_2$ (15 μm in thickness, weight ratio of 82:18) with 8.5% of carry rate. The open area of the catalyst was 63%, and the area available for contact with gas per volume (hereinafter referred to as Ap) was 795 m²/m³ The thickness of the $MnO_2$-$SiO_2$ layer was measured by electron probe micro analyzer (EPMA).

EXAMPLE 6

There was prepared a binary-catalyst carrying $MnO_2$-$SiO_2$ having 60% of open area and 775 m²/m³ of Ap, in the same manner as Example 5, except that carry weight of the catalyst was 41.3% and the average thickness was of the $MnO_2$-$SiO_2$ layer was about 50 μm in Example 6.

EXAMPLE 7

There was prepared a binary-catalyst carrying $MnO_2$-$SiO_2$ having 56% of open area and 750 m²/m³ of Ap, in the same manner as Example 5, except that the $MnO^2$-$SiO^2$ sol slurry was not diluted with water, that the average carry weight rate of the catalyst was 68.2%, and that the average thickness of the $MnO_2$-$SiO^2$ layer

TABLE 1

| | | REACTION CONDITIONS I | | REACTION CONDITIONS II | | REACTION CONDITIONS III | |
| --- | --- | --- | --- | --- | --- | --- | --- |
| | Malodorant Components | Rate of Removing Malodorant Components (%) | Ozone Residue (%) | Rate of Removing Malodorant Components (%) | Ozone Residue (%) | Rate of Removing Malodorant Components (%) | Ozone Residue (%) |
| Example 1 | H₂S | 91 | 0.8 | 93 | 0 | 91 | 0.6 |
| | NH₃ | 82 | 2.1 | 85 | 1.5 | 83 | 1.8 |
| | Methyl-mercaptan | 95 | 0 | 98 | 0 | 96 | 0 |
| Example 2 | H₂S | 94 | 0.2 | 95 | 0 | 94 | 0.2 |
| | NH₃ | 86 | 1.8 | 88 | 0.9 | 85 | 1.9 |
| | Methyl-mercaptan | 99 | 0 | 99 | 0 | 99 | 0 |
| Example 3 | H₂S | 94 | 0.1 | 98 | 0 | 93 | 0 |
| | NH₃ | 85 | 1.5 | 89 | 0.8 | 86 | 1.3 |
| | Methyl-mercaptan | 99 | 0 | 100 | 0 | 99 | 0 |
| Example 4 | H₂S | 98 | 0.5 | 94 | 0 | 94 | 0.1 |
| | NH₃ | 86 | 2.3 | 83 | 1.6 | 81 | 2.2 |
| | Methyl-mercaptan | 96 | 0 | 98 | 0 | 96 | 0 |
| Comparative Example 1 | H₂S | 76 | 3.5 | 79 | 3.0 | 77 | 3.1 |
| | NH₃ | 62 | 5.1 | 64 | 4.8 | 61 | 4.8 |
| | Methyl-mercaptan | 79 | 0.5 | 80 | 0.2 | 81 | 0.5 |
| Comparative Example 2 | H₂S | 98 | 0.2 | 100 | 0 | 77 | 0 |
| | NH₃ | 86 | 1.3 | 89 | 0 | 65 | 0 |
| | Methyl-mercaptan | 99 | 0 | 100 | 0 | 82 | 0 |

As apparent from Table 1, any of the catalysts obtained in Examples 1 to 4 present high and stable rates of removing malodorant components. Especially, those catalysts which were 10 to 200 μm in thickness of active components on a carrier, presented stable rates of removing malodorant components.

EXAMPLE 5

704 g of $MnO_2$, having 48 m²/g of specific surface area, was added to 77 ml of $SiO_2$ sol ($SiO_2$ concentration: 20% by weight). To the mixture, 250 g of glass beads were added to adjust the degree of milling. The resultant mixture was agitated and mixed for 30 minwas about 100 μm in this Example 7.

EXAMPLE 8

There was prepared a binary-catalyst carrying $MnO_2$-$SiO_2$ having 49% of open area and 700 m²/m³ of Ap, in the same manner as Example 5, except that the $MnO^2$-$SiO^2$ sol slurry was not diluted with water, that the carry weight rate of the catalyst was 82.5%, and that the average thickness of $MnO^2$-$SiO^2$ was about 200 μm in Example 8.

COMPARATIVE EXAMPLE 3

There was prepared a binary-catalyst carrying $MnO_2$-$SiO_2$ having 64% of open area and 798 $m^2/m^3$ of Ap, in the same manner as Example 5, except that the carry weight rate of the catalyst was 3.1% and the average thickness of the $MnO_2$-$SiO_2$ layer was about 5 $\mu m$ in this Comparative Example 3.

COMPARATIVE EXAMPLE 4

There was prepared a binary-catalyst carrying $MnO_2$-$SiO_2$ having 46% of open area and 675 $m^2/m^3$ of Ap, in the same manner as Example 5, except that the $MnO_2$-$SiO_2$ sol slurry was not diluted with water, that the carry weight rate of the catalyst was 98.4%, and that the average thickness of the $MnO_2$-$SiO_2$ layer was about 250 $\mu m$ in this Comparative Example 4.

Each of the catalysts obtained in Examples 5 to 8 and Comparative Examples 3 and 4 was examined as to catalyst activity in the same manner as Examples 1 to 5. The results are shown in Table 2.

EXAMPLE 10

There was prepared a binary-catalyst carrying a layer of $CuO$-$TiO_2$ (mol ratio of 24:76), having an average thickness of about 50 $\mu m$, with 91% of carry rate, in the same manner as Example 9, except that instead of 30 g of $MnO_2$, having 48 $m^2/g$ of specific surface area, used in Example 9, CuO, having 62 $m^2/g$ of specific surface area, was used in this Example 10.

EXAMPLE 11

There was prepared a binary-catalyst carrying a layer of $Co_3O_4$-$TiO_2$ (mol ratio of 24:76), having an average thickness of about 50 $\mu m$, with a 91% of carry rate, in the same manner as Example 9, except that, instead of 30 g of $MnO_2$, having 48 $m^2/g$ of specific surface area, used in Example 9, $Co_3O_4$, having 53 $m^2/g$ of specific surface area, was used in this Example 11.

EXAMPLE 12

There was prepared a binary-catalyst carrying a layer

TABLE 2

|  | Malodorant Components | REACTION CONDITIONS I | | REACTION CONDITIONS II | | REACTION CONDITIONS III | |
| --- | --- | --- | --- | --- | --- | --- | --- |
|  |  | Rate of Removing Malodorant Components (%) | Ozone Residue (%) | Rate of Removing Malodorant Components (%) | Ozone Residue (%) | Rate of Removing Malodorant Components (%) | Ozone Residue (%) |
| Example 5 | $H_2S$ | 94 | 0 | 96 | 0 | 94 | 0 |
|  | $NH_3$ | 79 | 3.5 | 80 | 1.8 | 79 | 3.8 |
|  | Methyl-mercaptan | 98 | 0 | 100 | 0 | 99 | 0 |
| Example 6 | $H_2S$ | 97 | 0 | 99 | 0 | 97 | 0 |
|  | $NH_3$ | 83 | 2.7 | 87 | 1.0 | 83 | 2.9 |
|  | Methyl-mercaptan | 100 | 0 | 100 | 0 | 100 | 0 |
| Example 7 | $H_2S$ | 97 | 0 | 100 | 0 | 97 | 0 |
|  | $NH_3$ | 82 | 2.1 | 86 | 1.3 | 83 | 2.0 |
|  | Methyl-mercaptan | 100 | 0 | 100 | 0 | 100 | 0 |
| Example 8 | $H_2S$ | 96 | 0 | 99 | 0 | 96 | 0 |
|  | $NH_3$ | 82 | 2.8 | 86 | 1.5 | 83 | 2.5 |
|  | Methyl-mercaptan | 100 | 0 | 100 | 0 | 100 | 0 |
| Comparative Example 3 | $H_2S$ | 79 | 3.8 | 81 | 2.9 | 65 | 8.7 |
|  | $NH_3$ | 66 | 5.7 | 65 | 5.3 | 54 | 10.6 |
|  | Methyl-mercaptan | 80 | 0.6 | 83 | 0.5 | 63 | 9.1 |
| Comparative Example 4 | $H_2S$ | 92 | 0.1 | 94 | 0 | 92 | 0.2 |
|  | $NH_3$ | 80 | 3.2 | 82 | 2.9 | 80 | 3.2 |
|  | Methyl-mercaptan | 96 | 0 | 98 | 0 | 96 | 0 |

As apparent from Tables 1 and 2, any of the catalysts obtained in Examples 1 to 6, that carried 10 to 200 $\mu m$ thick of active components on the carrier, presented high and stable rates of removing malodorant components.

EXAMPLE 9

30 g of $MnO_2$, having 48 $m^2/g$ of specific surface area, and 70 g of anatase type $TiO_2$, having 85 $m^2/g$ of specific surface area, were added to 170 ml of a titania sol ($TiO_2$ concentration: 150 g/l). The mixture was agitated and mixed for 30 minutes to produce a slurry, which was impregnated into a corrugated honeycomb made of ceramic fibers having 81% of open area and 4.0 mm of pitch. Thus, there was prepared a binary-catalyst carrying a layer of $MnO_2$-$TiO_2$ (mol ratio of 24:76) of average thickness of about 50 $\mu m$, with 101% of carry rate.

of $Fe_2O_3$-$TiO_2$ (mol ratio of 24:76), having an average thickness of about 50 $\mu m$, with a 78% of carry rate, in the same manner as Example 9, except that instead of 30 g of $MnO_2$, having 48 $m^2/g$ of specific surface area, used in Example 9, $Fe_2O_3$, having 53 $m^2/g$ of specific surface area, was used in this Example 12.

EXAMPLE 13

There was prepared 500 ml of a water solution containing 112 g of manganese acetate (4 hydrates), 182 g of cobalt nitrate (6 hydrates) and 63 g of metatitanic acid ($TiO_2$ concentration of 40%). While the solution was agitated, ammonia water was gradually added to the solution, causing the same to be neutralized. Thus, a slurry-like precipitate was produced with a final pH of 7.0. The slurry was impregnated into the same corrugated honeycomb as in Example 9 which then became impregnated with this precipitate. The impregnated honeycomb was calcined for three hours at 450° C. Thus, there was prepared a ternary-catalyst carrying $MnO_2$-$Co_3O_4$-$TiO_2$ (mol ratio of 25:50:25), of an average thickness of about 50 μm, with 89% of carry rate and having 72 m²/g of specific surface area.

EXAMPLE 14

There was prepared 500 ml of a water solution containing 17.8 g of manganese acetate (4 hydrates), 288 g of cobalt nitrate (6 hydrates) and 1.5g of silver nitrate. While the solution was agitated, a water solution of ammonium carbonate was added to the first mentioned solution, causing the same to be neutralized. thus, a slurry-like precipitate was produced with a final pH of 7.0. The slurry was impregnated into the same corrugated honeycomb as in Example 9. The impregnated honeycomb was then calcined for three hours at 450° C. Thus, there was prepared a ternary-catalyst carrying $Co_3O_4$-$MnO_2$-$TiO_2$ (mol ratio of 20:40:1), having an average thickness of about 50 μm, with a 92% of carry rate, and having 65% m²/g of specific surface area.

EXAMPLE 15

There was prepared 500 ml of a water solution containing 74.4 g of cupric nitrate (6 hydrates), 17.8 g of manganese acetate (4 hydrates) and 1.5 g of silver nitrate. While the solution was agitated, a water solution of ammonium carbonate was added to the first mentioned solution, causing the same to be neutralized. Thus, a slurry-like precipitate was produced with a final pH of 7.0. the slurry was impregnated into the same corrugated honeycomb as in Example 9. The impregnated honeycomb was then calcined for three hours at 450° C. Thus, there was prepared a ternary-catalyst carrying CuO-$MnO_2$-$Ag_2O$ (mol ratio of 20:40:1) having an average thickness of about 50 μm, with 87% of carry rate and having 71 m²/g of specific surface area.

EXAMPLE 16

There was prepared 500 ml of water solution containing 112 g of manganese acetate (4 hydrates), 195 g of nickel nitrate (6 hydrates) and 63 g of metatitanic acid ($TiO^2$ concentration of 40%). While the solution was agitated, ammonia water was gradually added to the solution. Thus, a slurry-like precipitate was produced with a final ph of 7.0. The slurry was impregnated into the same corrugated honeycomb as in Example 9. The impregnated honeycomb was then calcined for three hours at 450° C. Thus, there was prepared a ternary-catalyst carrying $MnO_2$-$Co^3O_4$-$TiO^2$ (mol ratio of 25:50:25) having an average thickness of about 50 μm, with 94% of carry rate, and having 80 m²/g of specific surface area.

EXAMPLE 17

There was prepared a ternary-catalyst carrying NiO-$MnO^2$-$TiO_2$ (mol ratio of 20:40:1) having an average thickness of about 50 μm with 98% of carry rate and having 77 m²/g of specific surface area, in the same manner as Example 14, except that instead of 288 g of cobalt nitrate (6 hydrates) used in Example 14, 309 g of Nickel nitrate (4 hydrates) was used in this Example 17.

EXAMPLE 18

There was prepared a binary-catalyst carrying $Fe^2O_3$-$Ag_2O$ (mol ratio of 95:5) having an average thickness of about 50 μm with 104% of carry rate, in the same manner as Example 9, except that instead of 70 g of the anatase type $TiO^2$ and 170 ml of a titania soluted used in Example 14, Au colloid, which was produced by adding 30% hydrogen peroxide to chloroauric acid at a pH of 8.0, was used in this Example 18.

COMPARATIVE EXAMPLE 5

30 g of $MnO_2$ having 48 m²/g of specific surface area and 70 g of a mixture ($MiO^2$:$SiO_2$=1:1) of titanium tetrachloride were mixed with a silica sol and were agitated. While agitating and mixing, ammonia gas was bubbled through the mixture such that the resultant mixture was neutralized, thereby to produce a slurry like precipitate. After being sufficiently washed with water, the precipitate was then calcined for three hours at 500° C. thus, there was prepared a ternary-catalyst carrying $MnO_2$-$TiO_2$-$SiO^2$ (mol ratio of 3:3.5:3.5) having 162 m²/g of specific surface area.

COMPARATIVE EXAMPLE 6

100 g of $TiO_2$ having 85 m²/g of specific surface area was calcined for three hours at 500° C. Thus, a catalyst which consisted of $TiO_2$ was obtained.

COMPARATIVE EXAMPLE 7

100 g of $MnO^2$ having 85 m²/g of specific surface area was baked for three hours at 500° C. Thus, a catalyst which consisted of $MnO_2$ was obtained.

Catalyst Activity Test

Each catalyst of Examples 9 to 18 and Comparative Examples 5 to 7 was submitted to a catalyst activity test by means of a test method according to the flowsheet as shown in FIG. 1, under reaction conditions described below.

| (Reaction Conditions) | |
| --- | --- |
| Space velocity | 20,000/Hr |
| Reaction Temperature | 20° C. |
| Malodorant Components | $H_2S$, $NH^3$ or mercaptan |

The test results are shown in Table 3.

TABLE 3

| | Malodorant Components | Concentration of Malodorant (ppm) | Concentration of Ozone (ppm) | Rate of Removing Malodorant Components (%) | Ozone Residue (%) |
| --- | --- | --- | --- | --- | --- |
| Example 9 | $H_2S$ | 10 | 20 | 98 | 0 |
| Example 10 | $H_2S$ | 10 | 20 | 91 | 2 |
| Example 11 | $H_2S$ | 10 | 20 | 86 | 3.2 |
| Example 12 | $H_2S$ | 10 | 20 | 98 | 0 |
| Example 13 | $H_2S$ | 10 | 20 | 99 | 0 |
| | $NH_3$ | 10 | 30 | 90 | 0.4 |
| | Methyl-mercaptan | 5 | 10 | 100 | 0 |
| Example 14 | $NH_3$ | 10 | 30 | 95 | 0 |
| Example 15 | $NH_3$ | 10 | 30 | 92 | 1.1 |
| Example 16 | $NH_3$ | 10 | 30 | 84 | 1.5 |

TABLE 3-continued

|  | Malodorant Components | Concentration of Malodorant (ppm) | Concentration of Ozone (ppm) | Rate of Removing Malodorant Components (%) | Ozone Residue (%) |
| --- | --- | --- | --- | --- | --- |
| Example 17 | $NH_3$ | 10 | 30 | 81 | 1.8 |
| Example 18 | $NH_3$ | 10 | 30 | 90 | 0.2 |
| Comparative Example 5 | $H_2S$ | 10 | 20 | 61 | 4.0 |
|  | $NH_3$ | 10 | 30 | 73 | 1.8 |
|  | Methyl-mercaptan | 5 | 10 | 88 | 1.0 |
| Comparative Example 6 | $H_2S$ | 10 | 20 | 12 | 72 |
|  | $NH_3$ | 10 | 30 | 8 | 89 |
|  | Methyl-mercaptan | 5 | 10 | 36 | 55 |
| Comparative Example 7 | $H_2S$ | 10 | 20 | 29 | 0 |
|  | $NH_3$ | 10 | 30 | 13 | 0 |
|  | Methyl-mercaptan | 5 | 10 | 49 | 0 |

As apparent from Table 3, any of the catalysts of Examples 9 to 18 showed a higher malodorant component removing rate than the catalysts of Comparative Examples 5 to 7.

Except for the catalyst of Example 9, any of the catalysts of Examples 9 to 18 showed a lower ozone residue than the catalysts of Comparative Examples 5 to 7.

EXAMPLE 19

704 g of $MnO_2$, having 48 m²/g of specific surface area, and 155 g of Kibushi clay were mixed with 1 l of water. To the mixture, 250 g of glass beads were added to adjust the degree of milling, and the mixture was agitated and mixed for 30 minutes to produce a slurry. After removing the glass beads the slurry was impregnated into a corrugated honeycomb made of ceramic fibers, having 81% open area and 4.0 mm of pitch. Thus, there was prepared a binary-catalyst carrying $MnO_2$-clay (weight ratio of 82:18) having an average thickness of about 50 μm with 95% of carry rate.

EXAMPLE 20

There was prepared a ternary-catalyst carrying $MnO_2$-$TiO_2$-clay (weight ratio of 82:9:9) having an average thickness of about 50 μm, with 95% of carry rate, in the same manner as Example 19, except that instead of 704 g of $MnO_2$ and 155 g of Kibushi clay mixed with 1 l of water used in Example 19, 78 g of Kibushi clay and 517 ml of titania sol ($TiO_2$ concentration : 150 g/l) was mixed with 500 ml of water in this Example 20.

EXAMPLE 21

There was prepared a binary-catalyst carrying $MnO_2$-clay (weight ratio of 24:76) having an average thickness of about 50 μm with 103% of carry rate, in the same manner as Example 19, except that instead of 704 g of $MnO_2$ and 155 g of Kibushi clay mixed with 1 l of water used in Example 19, 95 g of Kibushi clay and 30 g of $MnO_2$ were mixed with 500 ml of water in this Example 21.

EXAMPLE 22

There was prepared a ternary-catalyst carrying $MnO_2$-$TiO_2$-clay (weight ratio of 24:20:56) having an average thickness of about 50 μm with 101% of carry rate, in the same manner as Example 21, except that instead of 95 g of Kibushi clay and 30 g of $MnO_2$ mixed with 500 ml of water used in Example 21, 70 g of Kibushi clay, 30 g of $MnO^2$ and 170 ml of titania sol were mixed with 500 ml of water in this Example 22.

EXAMPLE 23

There was prepared ternary-catalyst carrying $MnO_2$-CuO-clay (weight ratio of 77:5:18) having an average thickness of about 50 μm with 97% of carry rate, in the same manner as Example 19, except that instead of 704 g of $MnO_2$ used in Example 19, 43 g of CuO and 661 g of $MnO_2$ were used in this Example 23.

EXAMPLE 24

There was prepared a ternary-catalyst carrying $MnO_2$-$Co^3O_4$-clay (weight ratio of 80:2:18) having an average thickness of about 50 μm with 101% of carry rate, in the same manner as Example 19, except that instead of 704 g of $MnO_2$ used in Example 19, 17 g of $Co_3O_4$ and 687 g of $MnO_2$ were used in this Example 24.

EXAMPLE 25

There was prepared a ternary-catalyst carrying $MnO_2$-$Fe_2O_3$-clay (weight ratio of 74:8:18) having an average thickness of about 50 μm with 98% of carry rate, in the same manner as in Example 19, except that instead of 704 g of $MnO_2$ used in Example 19, 70 g of $Fe_2O_3$ and 634 g of $MnO_2$ were used in this Example 25.

EXAMPLE 26

There was prepared a ternary-catalyst carrying $MnO_2$-NiO-clay (weight ratio of 76:6:18) having an average thickness of about 50 μm with 100% of carry rate, in the same manner as Example 19, except that instead of 704 g of $MnO_2$ used in Example 19, 50 g of NiO and 654 g of $MnO_2$ were used in this Example 26.

EXAMPLE 27

There was prepared a ternary-catalyst carrying $MnO^2$-$Ag^2O$-clay (weight ratio of 80:2:18) having an average thickness of about 50 μm with 100% of carry rate, in the same manner as Example 19, except that instead of 704 g of $MnO^2$ used in Example 19, 17 g of $Ag_2O$ and 687 g of $MnO^2$ were used in this Example 27.

EXAMPLE 28

There was prepared a quartery-catalyst carrying $MnO_2$-CuO-$TiO^2$-clay (weight ratio of 77:5:9:9) having an average thickness of about 50 μm with 103% of carry rate, in the same manner as Example 23, except that instead of 155 g of Kibushi clay used in Example 19, 78 g of Gairome clay and 517 g of titania sol were used in this Example 28.

EXAMPLE 29

There was prepared a quartery-catalyst carrying $MnO_2$-$Ag_2O$-$TiO_2$-clay (weight ratio of 80:2:9:9) having an average thickness of about 50 μm with 103% of carry rate, in the same manner as Example 19, except that instead of 155 g of Kibushi clay used in Example 19, 78 g of Gairome clay and 517 g of titania sol were used in this Example 29.

COMPARATIVE EXAMPLE 8

100 g of Kibushi clay, having 56 m²/g of specific surface area, was calcined for 3 hours at 500.C. Thus, a catalyst which consisted of Kibushi clay was obtained.

Catalyst Activity Test

Each catalyst of Example 19 to 29 and Comparative Example 8 were submitted to a catalyst activity test by means of a test method according to the flowsheet as shown in FIG. 1, under the same reaction conditions as Examples 9 to 18.

The test results are shown in Table 4.

Any of the catalysts obtained in Examples 19 to 29 showed a lower ozone residue than the catalyst obtained in Comparative Example 8.

EXAMPLE 30

After Gairome clay was dried for 18 hours at 100° C., it was crushed by a sample mill having a screen which has holes of 0.55 mm diameter. Then, 8 kg of the clay thus crushed was mixed with 2 kg of activated carbon, 0,8 kg of methyl cellulose type binder (Yuken Industry Co., YB-32) and water. The mixture was kneaded thoroughly by a kneader and put into an orga-screw type extruder to obtain a honeycomb. After being air-dried at ambient temperatures, the honeycomb was heated up to 500° C. at a rate of 5° C./hour and kept in that temperature for 3 hours. Then the honeycomb was cooled down at a rate of 10° C./hour. Thus, a honeycomb type carrier having 64% of open area and 1.0 mm of pitch was obtained.

Next, 500 ml of water and a small amount of binder were added to 1 kg of $MnO_2$, having 67 m²/g of specific surface area. By agitating this mixture for 30 minutes, bead was separated therefrom, to obtain slurry. The slurry was diluted with 300 ml of water, and this slurry

TABLE 4

| | Catalyst | Malodorant Components | Concentration of Malodorant (ppm) | Concentration of Ozone (ppm) | Rate of Removing Malodorant Components (ppm) | Ozone Residue (%) |
|---|---|---|---|---|---|---|
| Example 19 | $MnO_2$/ | $H_2S$ | 10 | 20 | 88 | 1.1 |
| | clay = | $NH_3$ | 10 | 30 | 82 | 1.4 |
| | 82/18 | Methyl-mercaptan | 5 | 10 | 98 | 0.5 |
| Example 20 | $MnO^2$/$TiO^2$/ | $H^2S$ | 10 | 20 | 90 | 0.8 |
| | clay = | $NH_3$ | 10 | 30 | 87 | 1.3 |
| | 82/9/9 | Methyl-mercaptan | 5 | 10 | 99 | 0.3 |
| Example 21 | $MNO_2$/ | $H^2S$ | 10 | 20 | 83 | 3.5 |
| | $TiO_2$ = | $NH_3$ | 10 | 30 | 83 | 1.6 |
| | 24/76 | Methyl-mercaptan | 5 | 10 | 95 | 0.5 |
| Example 22 | $MnO_2$/$TiO_2$/ | $H_2S$ | 10 | 30 | 85 | 1.5 |
| | clay = | $NH_3$ | 10 | 30 | 85 | 1.5 |
| | 24/20/56 | Methyl-mercaptan | 5 | 10 | 99 | 0.4 |
| Example 23 | $MnO_2$/CuO/ | $H_2S$ | 10 | 20 | 97 | 0 |
| | clay = | $NH_3$ | 10 | 30 | 90 | 0.4 |
| | 77/5/18 | Methyl-mercaptan | 5 | 10 | 98 | 0 |
| Example 24 | $MnO_2$/$Co_3O_4$/ | $H_2S$ | 10 | 20 | 98 | 0 |
| | clay = | $NH_3$ | 10 | 30 | 92 | 0.2 |
| | 80/2/18 | Methyl-mercaptan | 5 | 10 | 100 | 0 |
| Example 25 | $MnO_2$/$Fe_2O_3$/ | $H_2S$ | 10 | 20 | 99 | 0 |
| | clay = | $NH_3$ | 10 | 30 | 89 | 0 |
| | 74/8/18 | Methyl-mercaptan | 5 | 10 | 100 | 0.8 |
| Example 26 | $MnO_2$/NiO/ | $H_2S$ | 10 | 20 | 97 | 0 |
| | clay = | $NH_3$ | 10 | 30 | 91 | 0.5 |
| | 76/6/18 | Methyl-mercaptan | 5 | 10 | 100 | 0 |
| Example 27 | $MnO^2$/$Ag^2O$/ | $H^2S$ | 10 | 20 | 100 | 0 |
| | clay = | $NH_3$ | 10 | 30 | 93 | 1.5 |
| | 82/2/18 | Methyl-mercaptan | 5 | 10 | 100 | 0 |
| Example 28 | $MnO_2$/ | $H_2S$ | 10 | 20 | 99 | 0 |
| | CuO = | $NH_3$ | 10 | 30 | 93 | 0.2 |
| | 24/76 | Methyl-mercaptan | 5 | 10 | 100 | 0 |
| Example 29 | $MnO_2$/$Ag_2O$/ | $H_2S$ | 10 | 20 | 100 | 0 |
| | clay = | $NH_3$ | 10 | 30 | 94 | 0.3 |
| | 24/20/56 | Methyl-mercaptan | 5 | 10 | 100 | 0 |
| Comparative Example 8 | clay = 77/5/18 | $H_2S$ | 10 | 20 | 21 | 57 |
| | | $NH_3$ | 10 | 30 | 9 | 82 |
| | | Methyl-mercaptan | 5 | 10 | 40 | 30 |
| Example 24 | $MnO_2$/$Co_3O_4$/ | $H_2S$ | 10 | 20 | 98 | 0 |
| | clay = | $NH_3$ | 10 | 30 | 92 | 0.2 |
| | 80/2/18 | Methyl-mercaptan | 5 | 10 | 100 | 0 |
| Example 25 | $MnO_2$/$Fe_2O_3$/ | $H_2S$ | 10 | 20 | 99 | 0 |
| | clay = | $NH_3$ | 10 | 30 | 89 | 0 |
| | 74/8/18 | Methyl-mercaptan | 5 | 10 | 100 | 0.8 |

As apparent from Table 4, any of the catalysts obtained in Examples 19 to 29 show a higher removal rate of malodorant components than the catalyst of Comparative Example 8.

impregnated into honeycomb carrier, which been previously cut to the proper size. After removing the excessive slurry, the honeycomb carrier was dried, thereby to obtain a catalyst carrying $MnO_2$ having an average thickness of 31 μm. To determine the average thickness, the thickness was calculated by expressing n as 10 in linear analysis by means of EPMA. The thickness of the following examples was obtained in the same manner.

EXAMPLE 31

A binary-catalyst carrying $MnO_2$-$TiO_2$ (weight ratio of 80:20) was obtained in the same manner as Example 30, except that 200 g, out of the 1 kg of $MnO_2$ in Example 30, was substituted with $TiO_2$ and that 500 ml of water was used for dilution. By adjusting the number of times of coating, 5 types of catalysts having thicknesses, respectively, of 4 μm, 8 μm, 13 μm, 25 μm, and 38 μm were obtained.

EXAMPLE 32

A binary-catalyst carrying a layer of $MnO_2$-$Ag_2O$ (weight ratio of 90:10) having an average thickness of 43 μm was obtained in the same manner as Example 30, except that 100 g, out of the 1 kg of $MnO_2$ in Example 30, was substituted by $Ag_2O$.

EXAMPLE 33

A honeycomb shaped carrier was obtained in the same manner as Example 30, except that 5 kg of crushed Gairome clay, 5 kg of activated carbon, and 1 kg of methyl cellulose type binder (Yuken Industry, Co., YB-32) were used. The honeycomb was treated with the same slurry as in Example 31, and by adjusting the number of times of coating, 5 types of catalysts having thicknesses, respectively, of 5 μm, 10 μm, 18 μm, 29 μm and 43 μm were obtained.

EXAMPLE 34

A ternary-catalyst carrying a layer of $MnO_2$-$Fe_2O_3$-$Ag_2O$ (weight ratio of 50:40:10) having an average thickness of 50 μm was obtained in the same manner as Example 30, except that 400 g, out of 1 kg of $MnO_2$ in Example 30, was submitted by $Fe_2O_3$, having 38 $m^2/g$ of specific surface area, and 100 g, out of the above $MnO_2$, was substituted by $Ag_2O$.

EXAMPLE 35

A ternary-catalyst carrying a layer of $MnO_2$-(activated carbon)-$TiO_2$ (weight ratio of 70:20:10) having an average thickness of 38 μm was obtained in the same manner as Example 30, except that 200 g, out of 1 kg of $MnO_2$ in Example 30, was substituted by activated carbon (Takeda Chemical Industries, Ltd., Shirasagi-A) and 100 g, out of the above $MnO_2$, was substituted by $TiO_2$.

EXAMPLE 36

A catalyst carrying a layer of CuO having an average thickness of 49 μm was obtained in the same manner as Example 30, except that the $MnO_2$ in Example 30 was substituted by CuO, having 55 $m^2/g$ of specific surface area.

EXAMPLE 37

A catalyst carrying a layer of $MnO_2$ having an average thickness of 57 μm was obtained in the same manner as Example 33, except that 18 kg of Gairome clay and 2 kg of activated carbon were used in forming the carrier by extrusion.

COMPARATIVE EXAMPLE 9

A catalyst carrying a layer of $MnO_2$ having an average thickness of 50 μm, was obtained in the same manner as Example 30, except that 20 kg of Gairome clay was used, but activated carbon was not added in forming the carrier by extrusion.

REFERENCE EXAMPLE

There were mixed and agitated 30 g of $MnO_2$, having 48 $m^2/g$ of specific surface area, and 70 g of a mixture of titanium tetrachloride and silica sol ($TiO_2$:$SiO_2$=1). While agitating and mixing, ammonia gas was bubbled through the mixture in such a manner that the resultant mixture was neutralized, thereby to produce a slurry like precipitate. After being sufficiently washed with water, the precipitate thus produced was calcined for 3 hours at 500° C., and then was crushed. Thus, there was prepared a ternary-catalytic powder of $MnO_2$-$TiO_2$-$SiO_2$ (weight ratio of 35:30:35), having 162 $m^2/g$ of specific surface area. Then a ternary-catalyst carrying $SiO_2$-$MnO_2$-$TiO_2$ (weight ratio of 35:30:35) at 99% of carry rate was obtained in the same manner as Example 30.

Catalyst Activity Test

Each catalyst obtained in Examples 30 to 37 was submitted to a catalyst activity test by using a test apparatus, the flowsheet of which is shown in FIG. 1, and under the same reaction conditions as described below.

The ozone destruction rate (%) and the malodorant component destruction rate (%) were respectively calculated by using the following expression where the respective concentrations were measured by an ozone analyzer (3) and a malodorant component analyzer (4) at the inlet or the outlet of a catalytic layer (2) respectively:

$$\text{Destruction rate} = \frac{\text{Concentration at the inlet} - \text{Concentration at the outlet}}{\text{Concentration at the inlet}} \times 100$$

(Reaction Conditions)

| | |
|---|---|
| Space Velocity: | 20,000/Hr |
| Reaction temperature: | 20° C. |
| Ozone concentration at the inlet: | 10 ppm |
| Malodorant components: | methyl mercaptan, methyl amine, acetaldehyde, ammonia and hydrogen sulfide, in 5 ppm respectively |

Under such conditions, the ozone destruction rate and the malodorant component destruction rate were measured at the beginning of the test, after 10 hours and after 100 hours respectively, thereby to examine the deterioration of the catalyst. The results are shown in Table 5.

TABLE 5

| | Malodorant Components | | Destruction Rate (%) | | |
|---|---|---|---|---|---|
| | | | Beginning | After 10 Hr | After 100 Hr |
| Example 30 31 μm coating | Hydrogen sulfide | Ozone destruction rate | 99.8 | 99.8 | 97.6 |
| | | Malodorant component destruction rate | 99.4 | 99.2 | 94.8 |
| | Ammonia | Ozone | 99.9 | 99.9 | 98.3 |

TABLE 5-continued

| | Malodorant Components | | Destruction Rate (%) | | |
|---|---|---|---|---|---|
| | | | Beginning | After 10 Hr | After 100 Hr |
| | | destruction rate | | | |
| | | Malodorant component destruction rate | 73.7 | 71.8 | 54.3 |
| | Methyl amine | Ozone destruction rate | 99.8 | 99.8 | 97.8 |
| | | Malodorant component destruction rate | 96.2 | 95.5 | 85.3 |
| | Acetaldehyde | Ozone destruction rate | 99.9 | 99.8 | 98.0 |
| | | Malodorant component destruction rate | 99.1 | 98.9 | 93.8 |
| Example 31 4 μm coating | Acetaldehyde | Ozone destruction rate | 90.1 | 87.6 | 82.8 |
| | | Malodorant component destruction rate | 79.3 | 76.0 | 69.9 |
| 8 μm coating | Acetaldehyde | Ozone destruction rate | 99.4 | 98.1 | 94.9 |
| | | Malodorant component destruction rate | 97.1 | 93.3 | 86.8 |
| Example 31 13 μm coating | Acetaldehyde | Ozone destruction rate | 99.7 | 99.6 | 98.6 |
| | | Malodorant component destruction rate | 98.1 | 97.7 | 94.6 |
| 25 μm coating | Acetaldehyde | Ozone destruction rate | 100 | 99.8 | 99.1 |
| | | Malodorant component destruction rate | 99.0 | 98.7 | 96.0 |
| 38 μm coating | Acetaldehyde | Ozone destruction rate | 100 | 100 | 99.3 |
| | | Malodorant component destruction rate | 99.1 | 99.1 | 96.6 |
| Example 32 43 μm coating | Methylmercaptan | Ozone destruction rate | 99.9 | 99.9 | 99.5 |
| | | Malodorant component destruction rate | 96.6 | 96.4 | 92.7 |
| Example 33 5 μm coating | Methyl amine | Ozone destruction rate | 92.9 | 92.0 | 87.6 |
| | | Malodorant component destruction rate | 72.9 | 71.4 | 64.5 |
| 10 μm coating | Methyl amine | Ozone destruction rate | 99.8 | 99.8 | 96.7 |
| | | Malodorant component destruction rate | 95.0 | 94.8 | 81.5 |
| Example 33 18 μm coating | Methyl amine | Ozone destruction rate | 100 | 100 | 99.2 |
| | | Malodorant component destruction rate | 96.6 | 96.6 | 90.9 |
| 29 μm coating | Methyl amine | Ozone destruction rate | 100 | 100 | 99.6 |
| | | Malodorant component destruction rate | 97.7 | 97.6 | 93.4 |
| 43 μm coating | Methyl amine | Ozone destruction rate | 100 | 100 | 99.7 |
| | | Malodorant component destruction rate | 97.8 | 97.8 | 94.4 |
| Example 34 50 μm coating | Hydrogen sulfide | Ozone destruction rate | 99.8 | 92.9 | 84.6 |
| | | Malodorant component destruction rate | 99.4 | 87.6 | 77.3 |
| Example 35 38 μm coating | Hydrogen sulfide | Ozone destruction rate | 100 | 100 | 99.7 |
| | | Malodorant component destruction rate | 99.8 | 99.8 | 99.0 |
| | Methyl amine | Ozone destruction rate | 100 | 100 | 99.8 |
| | | Malodorant component destruction rate | 97.7 | 97.7 | 94.4 |
| Example 35 38 μm coating | Acetaldehyde | Ozone destruction rate | 100 | 100 | 99.7 |
| | | Malodorant component destruction rate | 99.4 | 99.3 | 98.1 |
| Example 36 49 μm coating | Acetaldehyde | Ozone destruction rate | 91.1 | 88.9 | 73.3 |
| | | Malodorant component destruction rate | 80.8 | 77.7 | 59.4 |
| Example 37 57 μm coating | Methyl amine | Ozone destruction rate | 97.3 | 95.9 | 88.9 |
| | | Malodorant component destruction rate | 83.4 | 79.4 | 77.7 |
| Comparative Example 9 50 μm coating | Methyl amine | Ozone destruction rate | 99.4 | 90.1 | 73.3 |
| | | Malodorant component destruction rate | 91.8 | 68.1 | 48.0 |
| Reference Example | Hydrogen sulfide | Ozone destruction rate | 98.4 | 61.3 | 40.4 |
| | | Malodorant component destruction rate | 96.9 | 51.7 | 32.0 |
| | Methyl amine | Ozone destruction rate | 97.2 | 57.6 | 29.1 |

TABLE 5-continued

| Malodorant Components | Destruction Rate (%) | | |
|---|---|---|---|
| | Beginning | After 10 Hr | After 100 Hr |
| Malodorant component destruction rate | 95.8 | 65.2 | 47.7 |

These results of the Catalyst Activity Test show that the catalyst of the present invention is effective to remove malodorant components at a high rate, and to leave little unreacted ozone after the deodorizing treatment.

EXAMPLE 38

30 g of $MnO_2$, having a specific surface area of 48 $m^2/g$, and 70 g of anatase type $TiO_2$, having a specific surface area of 85 $m^2/g$, were added to 170 ml of a titania sol ($TiO_2$ concentration: 150 g/l). The mixture was agitated and mixed for 30 minutes to produce a slurry, which was impregnated into a corrugated honeycomb made of ceramic fibers having an open area of 81% and a pitch of 4.0 mm. Thus, there was prepared a binary-catalyst carrying about 50 μm, in average thickness, of $MnO_2$-$TiO_2$ (mol ratio of 24:76) with a carry rate of 101%.

EXAMPLE 39

There was prepared a binary-catalyst carrying about 50 μm, in average thickness, of a layer of $CuO$-$TiO_2$ (mol ratio of 24:76) with a carry rate of 91%, in the same manner as that of Example 38, except that $CuO$, having a specific surface area of 62 $m^2/g$, was used in this Example 39, instead of 30 g of $MnO_2$, having a specific surface area of 58 $m^2/g$, which was used in Example 38.

EXAMPLE 40

There was prepared a binary-catalyst carrying about 50 μm in average thickness of $Co_3O_4$-$TiO_2$ (mol ratio of 24:76) with a carry rate of 91%, in the same manner as that of Example 38, except that $Co_3O_4$, having a specific surface area of 53 $m^2/g$, was used in this Example 40, instead of 30 g of $MnO_2$, having a specific surface area of 48 $m_2/g$, which was used in Example 38.

EXAMPLE 41 there was prepared a binary-catalyst carrying about 50 μm in average thickness of $Fe_2O_3$-$TiO^2$ (mol ratio of 24:76) with a carry rate of 78%, in the same manner as that of Example 38, except that $Fe_2O_3$, having a specific surface area of 53 $m^2/g$, was used in this Example 41, instead of 30 g of $MnO^2$, having a specific surface area of 48 $m^2/g$, which was used in Example 38.

EXAMPLE 42

There was prepared 500 ml of a water solution containing 112 g of manganese acetate (4 hydrates), 182 g of cobalt nitrate (6 hydrates) and 63 g of metatitanic acid ($TiO^2$ concentration of 40%). While the solution was agitated, ammonia water was gradually added to the solution, causing the same to be neutralized. Thus, a slurry-like precipitate was produced with a final pH of 7.0. The slurry was impregnated into the same corrugated honeycomb as in Example 38 which then became impregnated with this precipitate. The honeycomb was calcined for three hours at 450° C. Thus, there was prepared a ternary-catalyst carrying about 50 μm in average thickness of $MnO_2$-$Co_3O_4$-$TiO_2$ (mol ratio of 25:50:25) with a carry rate of 89% and having a specific surface area of 72 $m^2/g$.

EXAMPLE 43

There was prepared 500 ml of a water solution containing 17.8 g of manganese acetate (4 hydrates), 288 g of cobalt nitrate (6 hydrates) and 1.5 g of silver nitrate. While the solution was agitated, a water solution of ammonium carbonate was added to the first mentioned solution, causing the same to be neutralized. Thus, a slurry-like precipitate was produced with a final pH of 7.0. The slurry was impregnated into the same corrugated honeycomb as in Example 38. The honeycomb was then calcined for three hours at 450° C. Thus, there was prepared a ternary-catalyst carrying about 50 μm in average thickness of $Co_3O_4$-$MnO_2$-$TiO_2$ (mol ratio of 20:40:1) with a carry rate of 92% and having a specific surface area of 65 $m^2/g$.

EXAMPLE 44

There was prepared 500 ml of a water solution containing 74.4 g of cupric nitrate (6 hydrates), 17.9 g of manganese acetate (4 hydrates) and 1.5 g of silver nitrate. While the solution was agitated, a water solution of ammonium carbonate was added to the first mentioned solution, causing the same to be neutralized. Thus, a slurry like precipitate was produced with a final pH of 7.0. This slurry was impregnated into the same corrugated honeycomb as in Example 38. The honeycomb was then calcined for three hours at 450.C. Thus, there was prepared a ternary-catalyst carrying about 50 μm in average thickness of $CuO$-$MnO^2$-$Ag_2O$ (mol ratio of 20:40:1) with a carry rate of 87% and having a specific surface area of 71 $m^2/g$.

EXAMPLE 45

There was prepared 500 ml of a water solution containing 112 g of manganese acetate (4 hydrates), 195 g of nickel (6 hydrates) and 63 g of metatitanic acid ($TiO_2$ concentration of 40%). While the solution was agitated, ammonia water was gradually added to the solution. Thus, a slurry-like precipitate was produced with a final pH of 7.0. The slurry was impregnated into the same corrugated honeycomb as in Example 38. The honeycomb was calcined for three hours at 450.C. Thus, there was prepared a ternary-catalyst carrying about 50 μm in average thickness of $MnO_2$-$Co_3O_4$-$TiO_2$ (mol having a specific surface area of 80 $m^2/g$.

EXAMPLE 46

There was prepared a ternary-catalyst carrying about 50 μm in average thickness of $NiO$-$MnO_2$-$TiO_2$ (mol ratio of 20:40:1) with a specific surface area of 77 $m^2/g$, and a carry rate of 98%, in the same manner of Example 43, except that 309 g of a nickel nitrate (4 hydrates) used in this Example 46 instead of 288 g of cobalt nitrate (6 hydrates) in Example 43.

EXAMPLE 47

There was prepared a binary-catalyst carrying about 50 μm in average thickness of $Fe^2O_3$-$Ag_2O$ (mol ratio of 95:5) with a carry rate of 104%, in the same manner of Example 38, except that a Au colloid, which was produced by adding 30% hydrogen peroxide to chloroauric acid at a pH of 8.0, was used in Example 16, instead of 70 g of anatase type $TiO_2$ and 170 ml of a titania solution used in Example 43.

COMPARATIVE EXAMPLE 10

30 g of $MnO_2$ having a specific surface area of 48 m$^2$/g, and 70 g of a mixture ($MiO_2:SiO_2 = 1:1$) of titanium tetrachloride with a silica sol were agitated and mixed. While agitating and mixing, ammonia gas was bubbled through such that the resultant mixture was neutralized, thereby to produce a slurry-like precipitate. After being sufficiently washed with water, the precipitate was then calcined for three hours at 500° C. Thus, there was prepared a ternary catalyst $MnO_2$-$TiO_2$-$SiO_2$ (mol ratio of 3:3.5:3.5) having a specific surface area of 162 m$^2$/g.

COMPARATIVE EXAMPLE 11

100 g of $TiO_2$ having a specific surface area of 85 m$^2$/g was calcined for 3 hours at 500° C. Thus, a catalyst which consisted of $TiO_2$ was obtained.

COMPARATIVE EXAMPLE 12

100 g of $MnO_2$ having a specific surface area of 85 m$^2$/g was baked for 3 hours at 500° C. Thus, a catalyst which consisted of $MnO_2$ was obtained

Catalyst Activity Test

Each catalyst of Examples 38 to 47 and Comparative Examples 10 to 12 was submitted to a catalyst activity test with the use of the test method according to the flowsheet as shown in FIG. 1, under reaction conditions discussed later.

| (Reaction Conditions) | |
|---|---|
| Space Velocity | 20,000/Hr |
| Reaction temperature | 20° C. |
| Malodorant components | $H_2S$, $NH_3$ or methyl mercaptan |

The test results are shown in the following Table 6.

rant component removing rate than the catalysts obtained in Comparative Examples 9 to 11.

Except for the catalyst of Example 38, any of the catalysts obtained in Examples 38 to 47 shows a lower ozone residue than the catalysts obtained in Comparative Examples 10 to 12.

EXAMPLE 48

704 g of $MnO_2$, having a specific surface area of 48 m$^2$/g, and 155 g of Kibushi clay were mixed with 1 l of water. To the mixture, 250 g of glass beads were added to adjust the degree of milling, and was agitated and mixed for 30 minutes to produce a slurry. After removing the glass beads, the slurry was impregnated into a corrugated honeycomb made of ceramic fibers having an open area rate of 81% and pitch of 4.0 mm. Thus, there was prepared a binary-catalyst carrying about 50 μm in average thickness of $MnO_2$-clay (weight rate of 82:18) with a carry rate of 95%.

EXAMPLE 49

There was prepared a ternary-catalyst carrying about 50 μm in average thickness of $MnO_2$-$TiO_2$-clay (weight rate of 82:9:9) with a carry rate of 95%, in the same manner as that of Example 48, except that 78 g of Kibushi clay and 517 ml of titania sol ($TiO_2$ concentration: 150 g/l) was mixed with 500 ml of water in this Example 49, instead of 704 g of $MnO_2$ and 155 g Kibushi clay mixed with 1 l of water in Example 17.

EXAMPLE 50

There was prepared a binary-catalyst carrying 50 μm in average thickness of $MnO_2$-clay (weight ratio of 24:76) with a carry rate of 103%, in the same manner as that set forth in Example 48, except that 95 g of Kibushi clay and 30 g of $MnO_2$ were mixed with 500 ml of water in this Example 50, instead of the 704 g of $MnO_2$ and 155 g Kibushi clay mixed with 1 l of water in Example 48.

TABLE 6

| | Malodorant Components | Concentration of Malodorant Components (ppm) | Concentration of Ozone (ppm) | Rate of Removing Malodorant Components (%) | Ozone Residue (%) |
|---|---|---|---|---|---|
| Example 38 | $H_2S$ | 10 | 20 | 98 | 0 |
| Example 39 | $H_2S$ | 10 | 20 | 91 | 2 |
| Example 40 | $H_2S$ | 10 | 20 | 86 | 3.2 |
| Example 41 | $H_2S$ | 10 | 20 | 98 | 0 |
| Example 42 | $H_2S$ | 10 | 20 | 99 | 0 |
| | $NH_3$ | 10 | 30 | 90 | 0.4 |
| | Methyl-mercaptan | 5 | 10 | 100 | 0 |
| Example 43 | $NH_3$ | 10 | 30 | 95 | 0 |
| Example 44 | $NH_3$ | 10 | 30 | 92 | 1.1 |
| Example 45 | $NH_3$ | 10 | 30 | 84 | 1.5 |
| Example 46 | $NH_3$ | 10 | 30 | 81 | 1.8 |
| Example 47 | $NH_3$ | 10 | 30 | 90 | 0.2 |
| Comparative Example 10 | $H_2S$ | 10 | 20 | 61 | 4.0 |
| | $NH_3$ | 10 | 30 | 73 | 1.8 |
| | Methyl-mercaptan | 5 | 10 | 88 | 1.0 |
| Comparative Example 11 | $H_2S$ | 10 | 20 | 12 | 72 |
| | $NH_3$ | 10 | 30 | 8 | 89 |
| | Methyl-mercaptan | 5 | 10 | 36 | 55 |
| Comparative Example 12 | $H_2S$ | 10 | 20 | 29 | 0 |
| | $NH_3$ | 10 | 30 | 13 | 0 |
| | Methyl-mercaptan | 5 | 10 | 49 | 0 |

As apparent from Table 6, any of the catalysts obtained in Examples 38 to 47 presents a higher malodo-

EXAMPLE 51

There was prepared a ternary-catalyst carrying 50 μm in average thickness of $MnO_2$-$TiO_2$-clay (weight ratio of 24:20:56) with a carry rate of 101%, in the same manner as the Example 50, except that 70 g of Kibushi clay, 30 g of $MnO_2$ and 170 ml of titania sol was mixed with 500 ml of water in this Example 51, instead of 95 g of Kibushi clay and 30 g of $MnO_2$ mixed with 500 ml of water in Example 50.

EXAMPLE 52

There was prepared a ternary-catalyst carrying 50 μm in average thickness of $MnO_2$-CuO-clay (weight ratio of 77:5:18) with a carry rate of 97%, in the same manner as that Example 48, except that 43 g of CuO and 661 g of $MnO_2$ used in this Example 52, instead of 704 g of $MnO_2$ used in Example 48.

EXAMPLE 53

There was prepared a ternary-catalyst carrying 50 μm in average thickness of $MnO_2$-$Co_3O_4$-clay (weight ratio of 80:2:18) with a carry rate of 101%, in the same manner as that Example 48, except that 17 g of $Co_3O_4$ and 687 g of $MnO_2$ used in this Example 53, instead of 704 g of $MnO_2$ used in Example 48.

EXAMPLE 54

There was prepared a ternary-catalyst carrying 50 μm in average thickness of $MnO_2$-$Fe_2O_3$-clay (weight ratio of 74:8:18) with a carry rate of 98%, in the same manner as that Example 48, except that 70 g of $Fe_2O_3$ and 634 g of $MnO_2$ used in this Example 54, instead of 704 g of $MnO_2$ used in Example 48.

EXAMPLE 55

There was prepared a ternary-catalyst carrying 50 μm in average thickness of $MnO_2$-NiO-clay (weight ratio of 76:6:18) with a carry rate of 100%, in the same manner as that Example 48, except that 50 g of NiO and 654 g of $MnO_2$ used in this Example 55, instead of 704 g of $MnO_2$ used in Example 48.

EXAMPLE 56

There was prepared a ternary-catalyst carrying 50 μm in average thickness of $MnO_2$-$Ag_2O$-clay (weight ratio of 80:2:18) with a carry rate of 100%, in the same manner as that Example 48, except that 17 g of $Ag_2O$ and 687 g of $MnO_2$ used in this Example 56, instead of 704 g of $MnO_2$ used in Example 48.

EXAMPLE 57

There was prepared a quartery-catalyst carrying 50 μm in average thickness of $MnO_2$-CuO-$TiO_2$-clay (weight ratio of 77:5:9:9) with a carry rate of 103%, in the same manner as that Example 52, except that 78 g of Gairome clay and 517 g of titania sol used in this Example 57, instead of 155 g of Kibushi clay used in Example 48.

EXAMPLE 58

There was prepare a quartery-catalyst carrying 50 μm in average thickness of $MnO_2$-$Ag_2O$-$TiO_2$-clay (weight ratio of 80:2:9:9) with a carry rate of 103%, in the same manner as that Example 48, except that 78 g of Gairome clay and 517 g of titania sol used in this Example 58, instead of 155 g of Kibushi clay in Example 48.

COMPARATIVE EXAMPLE 13

100 g of Kibushi clay having a specific surface area of 56 $m^2$/g was calcined for 3 hours at 500° C. Thus, a catalyst consisting of Kibushi clay, was obtained.

Catalyst Activity Test

Each catalyst of Examples 48 to 58 and Comparative Example 13 were submitted to a catalyst activity test using the test method according to the flowsheet as shown in FIG. 1, under the same reaction conditions as the Examples 38 to 47.

The test results are shown in Table 7.

TABLE 7

| | Catalyst | Malodorant Components | Concentration of Malodorant Components (ppm) | Concentration of Ozone (ppm) | Rate of Removing Malodorant Components (ppm) | Ozone Residue (%) |
|---|---|---|---|---|---|---|
| Example 48 | $MnO_2$/ clay = 82/18 | $H_2S$ | 10 | 20 | 88 | 1.1 |
| | | $NH_3$ | 10 | 30 | 82 | 1.4 |
| | | Methyl-mercaptan | 5 | 10 | 98 | 0.5 |
| Example 49 | $MnO_2$/$TiO_2$/ clay = 82/9/9 | $H_2S$ | 10 | 20 | 90 | 0.8 |
| | | $NH_3$ | 10 | 30 | 87 | 1.3 |
| | | Methyl-mercaptan | 5 | 10 | 99 | 0.3 |
| Example 50 | $MnO_2$/$TiO_2$/ clay = 24/76 | $H_2S$ | 10 | 20 | 83 | 3.5 |
| | | $NH_3$ | 10 | 30 | 83 | 1.6 |
| | | Methyl-mercaptan | 5 | 10 | 95 | 0.5 |
| Example 51 | $MnO_2$/$TiO_2$/ clay = 24/20/56 | $H_2S$ | 10 | 20 | 85 | 2.8 |
| | | $NH_3$ | 10 | 30 | 85 | 1.5 |
| | | Methyl-mercaptan | 5 | 10 | 99 | 0.4 |
| Example 52 | $MnO_2$/CuO/ clay = 77/5/18 | $H_2S$ | 10 | 20 | 97 | 0 |
| | | $NH_3$ | 10 | 30 | 90 | 0.4 |
| | | Methyl-mercaptan | 5 | 10 | 98 | 0 |
| Example 53 | $MnO_2$/$Co_3O_4$/ clay = 80/2/18 | $H_2S$ | 10 | 20 | 98 | 0 |
| | | $NH_3$ | 10 | 30 | 92 | 0.2 |
| | | Methyl-mercaptan | 5 | 10 | 100 | 0 |
| Example 55 | $MnO_2$/NiO/ clay = 76/6/18 | $H_2S$ | 10 | 20 | 97 | 0 |
| | | $NH_3$ | 10 | 30 | 91 | 0.5 |
| | | Methyl-mercaptan | 5 | 10 | 100 | 0 |
| Example 56 | $MnO_2$/$Ag_2O$/ clay = 82/8/18 | $H_2S$ | 10 | 20 | 100 | 0 |
| | | $NH_3$ | 10 | 30 | 93 | 0.5 |
| | | Methyl-mercaptan | 5 | 10 | 100 | 0 |
| Example 57 | $MnO_2$/CuO/ $TiO_2$/ clay = 80/2/9/9 | $H_2S$ | 10 | 20 | 99 | 0 |
| | | $NH_3$ | 10 | 30 | 93 | 0.2 |
| | | Methyl-mercaptan | 5 | 10 | 100 | 0 |
| Example 58 | $MnO_2$/$Ag_2O$/ | $H_2S$ | 10 | 20 | 100 | 0 |

TABLE 7-continued

|  | Catalyst | Malodorant Components | Concentration of Malodorant Components (ppm) | Concentration of Ozone (ppm) | Rate of Removing Malodorant Components (ppm) | Ozone Residue (%) |
|---|---|---|---|---|---|---|
|  | $TiO_2$/ clay = 80/2/9/9 | $NH_3$ Methyl-mercaptan | 10 5 | 30 10 | 94 100 | 0.3 0 |
| Comparative Example 13 | clay | $H_2S$ $NH_3$ Methyl-mercaptan | 10 10 5 | 20 30 10 | 21 30 10 | 57 82 30 |

As apparent from Table 7, any of the catalysts obtained in Example 48 to 58 presents a higher removing rate of malodorant components than that of the catalysts obtained in Comparative Example 1 to 4.

And any of the catalysts obtained in Example 48 to 58 presents a lower ozone residue than that of the catalysts obtained in Comparative Example 1 to 4.

These results of the Catalyst Activity Test show that the method of the present invention is effective to remove malodorant components at a high rate, and that unreacted ozone does not substantially remain after the deodorizing treatment.

What is claimed is:

1. A catalyst for use in a deodorizing method for removing malodorant components by oxidative destruction with ozone, the catalyst comprising a carrier and active components carried on said carrier in a thickness in the range of from 10 to 200 μm, the active components for promoting the reaction of the malodorant components with said ozone comprising (i) about 20 to 90 per cent by weight of manganese dioxide; and (ii) clay.

2. A catalyst, for use in said deodorizing method, according to claim 1, wherein said catalyst comprises titanium dioxide in addition to said manganese dioxide and clay.

3. A catalyst, for use in said deodorizing method according to claim 1, wherein said catalyst comprises 1 to 30% of weight at least one metal oxide, the metal of which is selected from a group consisting of Cu, Co, Ni and Ag, in addition to said manganese dioxide and clay.

4. A catalyst for use in a deodorizing method for removing malodorant components by oxidative destruction with ozone, which comprises a carrier containing at least about 10% by weight of activated carbon, and active components disposed on said carrier in a thickness in the range of from 5 to 100 μm, the active components comprising at least one metal, metal oxide or metal sulfate, the metal of which is selected from the group consisting of Ti, Cu, Mn, Ni, Fe, Ag, Au, Mo, Zr, Sn, Nb, and W.

5. A catalyst, for use in said deodorizing method, according to claim 4, wherein the thickness of said active components is 10 to 50 μm.

6. A catalyst for use in a deodorizing method for removing malodorant components by oxidative destruction with ozone, the catalyst comprising a carrier and active components carried on said carrier in a thickness in the range of from 10 to 200 μm, the active components for promoting the reaction of the malodorant components with said ozone comprising (i) 25 to 95 weight per cent, based on metal, of at least one metal oxide, the metal of which is selected from the group consisting of Cu, Co, Mn, Mi and Fe; and (ii) 5 to 7 weight per cent, based on metal, of at least one member selected from the group consisting of titanium dioxide, silver oxide and gold, or an amount of silica which is sufficient to promote the destruction of malodorant components by reaction with ozone.

7. A catalyst for use in deodorizing method, according to claim 6, comprising as active components, at least one of $MnO_2$-$TiO_2$, $CuO$-$TiO_2$, $Co_3O_4$-$TiO_2$, $Fe_2O_3$-$TiO_2$, $Fe_2O_3$-$Au$, $CuO$-$MnO_2$-$Ag_2O$, $MnO_2$-$Co_3O_4$-$TiO_2$, $MnO_2$-$Co_3O_4$-$Ag_2O$, $NiO$-$MnO_2$-$TiO_2$, or $MnO_2$-$SiO_2$.

8. A catalyst for use in the deodorizing method according to claim 6, wherein the concentration of said active components in said catalyst is at least 50 per cent by weight.

* * * * *

UNITED STATES PATENT AND TRADEMARK OFFICE
CERTIFICATE OF CORRECTION

PATENT NO. : 5,214,014
DATED : May 25, 1993
INVENTOR(S) : Masafumi Yoshimoto et al It is certified that error appears in the above-indentified patent and that said Letters Patent is hereby corrected as shown below:

On the title page, Item [63], change "Oct. 10, 1989" to --September 25, 1989--.

Signed and Sealed this

Twenty-eighth Day of December, 1993

Attest:

BRUCE LEHMAN

*Attesting Officer*  *Commissioner of Patents and Trademarks*